| United States Patent [19] | [11] | Patent Number: | 4,889,955 |
|---|---|---|---|
| Ranken | [45] | Date of Patent: | Dec. 26, 1989 |

[54] PREPARATION OF (HYDROCARBYLTHIO)AROMATIC AMINES

[75] Inventor: Paul F. Ranken, Baton Rouge, La.

[73] Assignee: Ethyl Corporation, Richmond, Va.

[21] Appl. No.: 270,819

[22] Filed: Nov. 14, 1988

Related U.S. Application Data

[63] Continuation-in-part of Ser. No. 917,169, Oct. 9, 1986, abandoned, which is a continuation-in-part of Ser. No. 624,532, Jun. 25, 1984, abandoned.

[51] Int. Cl.$^4$ .................... C07C 149/42; C07C 87/64; C07D 209/36; C07D 233/66
[52] U.S. Cl. .................................. 564/440; 564/315; 564/426; 564/427; 564/428; 564/430; 546/290; 548/337; 548/484; 548/541; 568/38
[58] Field of Search ............... 564/315, 426, 430, 440, 564/427, 428; 568/38; 546/290; 548/337, 484, 541

[56] References Cited

PUBLICATIONS

Fujisawa et al., "Rearrangement of Aryl Sulfides in the Presence of Aluminum Chloride", *Bull. Chem. Soc. Jap.*, Vol. 43, pp. 1189–1196, (1970).

*Primary Examiner*—Glennon H. Hollrah
*Assistant Examiner*—Peter G. O'Sullivan
*Attorney, Agent, or Firm*—Patricia J. Hogan

[57] ABSTRACT ar-(Hydrocarbylthio)aromatic amines, such as (alkylthio) anilines, are prepared by heating one or more other ar-(hydrocarbylthio)aromatic amines in the presence of a catalyst, such as aluminum chloride, to redistribute the hydrocarbylthio groups with little or no co-formation of secondary or tertiary amines. The amine starting material is one or more primary aromatic amines having at least one free ring position and at least one hydrocarbylthio substituent in a ring position other than a meta-position.

12 Claims, No Drawings

PREPARATION OF (HYDROCARBYLTHIO)AROMATIC AMINES

CROSS-REFERENCE TO RELATED APPLICATION

This application is a continuation-in-part of copending application Ser. No. 917,169, filed Oct. 9, 1986, which in turn is a continuation-in-part of Ser. No. 624,532, filed June 25, 1984 both of which applications are, now abandoned.

FIELD OF INVENTION

The invention relates to ar-(hydrocarbylthio)aromatic amines and more particularly to a process for preparing them by the redistribution of hydrocarbylthio groups in other ar-(hydrocarbylthio)aromatic amines.

BACKGROUND

As disclosed in U.S. Pat. No. 4,594,453 (Ranken et al.), it is known that various ar-(hydrocarbylthio)aromatic amines are useful as intermediates in the preparation of biologically-active materials, polyurethanes, etc., and that they can be prepared by reacting appropriate aromatic amines with hydrocarbyl disulfides in the presence of suitable catalysts, such as aluminum chloride. Unfortunately, these syntheses typically result in the formation of mixtures of ar-(hydrocarbylthio)aromatic amines.

U.S. Pat. No. 4,547,593 (Ranken) teaches that particular (hydrocarbylthio)phenols can be prepared by heating other (hydrocarbylthio)phenols in the presence of an aluminum phenoxide catalyst to redistribute the hydrocarbylthio groups.

Fujisawa et al., *Bulletin of the Chemical Society of Japan*, Vol. 43, No. 4, 1970, pp. 1189–1196, teach that arylthio substituents in o-, m-, and p-tolyl phenyl sulfides can be rearranged in the presence of aluminum chloride. Han et al., *Tetrahedron Letters*, No. 30, pp. 2629–2632, 1970, also teach that arylthio substituents in aromatic hydrocarbons can be rearranged with aluminum chloride, presumably by sulfonium ion formation, ring thiation, and subsequent proton loss.

The redistribution of hydrocarbylthio groups on an aromatic ring containing an amino group, however, is not expected. March, *Advanced Organic Chemistry*, Second Edition, McGraw-Hill, New York, page 486, teaches that amino groups are very reactive toward Lewis acids such as aluminum bromide and aluminum chloride. Their presence on an aromatic ring inhibits the catalytic activity that the Lewis acid would otherwise have in electrophilic aromatic substitution reactions such as Friedel-Craft alkylations. The inhibition of the catalytic activity of the Lewis acids by the amino group, particularly when ether and sulfides are involved, is due to the strong complexation of the amino group with the Lewis acid. Oae, *Organic Chemistry of Sulfur*, Plenum Press, New York, page 251, teaches that the order of bond strength for the complexation of compounds with an aluminum halide is amines>ethers>sulfides. The reaction of (hydrocarbylthio)aromatic amines with aluminum chloride would thus be expected to give products involving the nitrogen rather than the sulfur. Typical reactions would be the formation of diarylamines as taught by Thomas, *Anhydrous Aluminum Chloride in Organic Chemistry*, Reinhold Publishing Corporation, New York, pp. 156–157, 1941.

SUMMARY OF INVENTION

An object of this invention is to provide a novel process for preparing ar-(hydrocarbylthio)aromatic amines.

Another object is to provide such a process wherein the (hydrocarbylthio)aromatic amines are prepared by the redistribution of hydrocarbylthio groups in other ar-(hydrocarbylthio)aromatic amines.

These and other objects are attained by heating one or more primary aromatic amines having at least one free ring position and at least one hydrocarbylthio substituent in a ring position other than a position meta to the amino group in the presence of a catalyst to redistribute the hydrocarbylthio groups with little or no co-formation of secondary or tertiary amines.

DETAILED DESCRIPTION

Aromatic amines useful as starting materials in the practice of the invention are primary aromatic amines having one or more hydrocarbylthio groups attached to an aromatic ring which may bear one or more inert substituents, i.e., substituents inert to the reaction conditions, in positions unsubstituted by amino or hydrocarbylthio groups, as long as at least one ring position remains free.

When the aromatic amine is a compound which has metapositions, i.e., a carbocyclic aromatic amine, it may bear metahydrocarbylthio substituents. However, since the process is not very effective in redistributing meta-hydrocarbylthio substituents to other positions, such substituents may not be the only hydrocarbylthio substituents in the starting material. Either the aromatic amine which bears the meta-hydrocarbylthio substituent must bear other hydrocarbylthio substituents, or it must be used in admixture with another aromatic amine which bears at least one hydrocarbylthio substituent in a position other than a meta-position.

When the aromatic amine starting material is a mixture of aromatic amines, it is not essential that the free position and hydrocarbylthio substituent requirements be satisfied in the same aromatic amine molecule. For example, it is within the scope of the invention for the starting material to be a mixture of aniline and a fully-substituted (hydrocarbylthio)aniline.

Aromatic amines which can serve as components of the starting material and/or as the amine substrates of the (hydrocarbylthio)aromatic amines may be mono- or polynuclear aromatic amines, such as the aromatic amines taught in Ranken et al., the teachings of which are incorporated herein toto by reference. In general, these aromatic amines are:

(1) compounds having at least one amino group attached to a carbocyclic or heterocyclic ring of an aromatic compound containing one or more simple and/or fused rings, such as benzene, naphthalene, anthracene, pyrrole, pyridine, indole, etc., rings or (2) reactive heterocyclic amines, such as pyrrole, indole, imidazole, etc., optionally bearing substituents inert to the reaction conditions, such as one or more additional amino groups or substituents such as chloro, fluoro, alkyl, aryl, alkaryl, or aralkyl groups. In the case of coupled aromatic rings, the rings may be directly attached to one another or may be coupled through a bridge such as an oxygen, sulfur, sulfoxide, sulfone, alkyl, or other hydrocarbon link.

Examples of such aromatic amines are 4,4-methylenedianiline, 4-(phenylthio)aniline, 1,3-dimethylpyrrole, 1-methylpyrrole, 2-aminobiphenyl, 7-methylindole, aminobenzenes containing one or two amino groups, such as aniline, 4-butylaniline, 4-methylaniline, 4-chloroaniline, 2-ethylaniline, 2,4- and 2,6-diaminotoluenes, 2,6-diamino-1-ethylbenzene, etc.

As in Ranken et al., the hydrocarbylthio groups of the (hydrocarbylthio)aromatic amines may be aliphatic, cycloaliphatic, or aromatic, such as methylthio, ethylthio, butylthio, cyclopentylthio, cyclohexylthio, benzylthio, p-tolylthio, p-chlorophenylthio, etc.; but they are preferably alkylthio groups, most preferably alkylthio groups containing 1–6 carbons. When they re attached to the ring of a carbocyclic aromatic amine, those in the para-position are redistributed most extensively.

Catalysts that can be used in the practice of the invention are generally the same as the catalysts employed by Ranken et al., i.e., Lewis acid catalysts, such as metal halides, e.g., aluminum chloride, boron trifluoride, ferric chloride, zinc chloride, etc.; metal alkyls, e.g., triethylaluminum, diethylaluminum chloride, ethyl aluminum dichloride, etc.; and the organometallic compounds derived from the reaction of an aromatic amine with the metal halides, metal alkyls, and reactive metals such as aluminum. The preferred catalysts are the metal halides, such as aluminum chloride, boron trifluoride, and boron trichloride, with aluminum chloride being especially preferred.

The process of the invention is conducted by contacting the aromatic amine starting material with a catalytic amount, e.g., about 0.01–0.5, preferably about 0.01–0.2, mol of the catalyst per mol of the aromatic amine, and heating the reaction mixture at a suitable temperature, e.g., about 100–300° C., until the hydrocarbylthio groups have been redistributed and the desired (hydrocarbylthio)aromatic amine has been formed. As indicated above, this formation of the desired compound may proceed by intramolecular redistribution or by intermolecular redistribution and, in the case of intermolecular redistribution, may involve transferring hydrocarbylthio groups from one (hydrocarbylthio)aromatic amine to another (hydrocarbylthio)aromatic amine or to an aromatic amine which was originally free of hydrocarbylthio substituents. The transfer to an aromatic amine which is originally free of hydrocarbylthio substituents is of particular value when it is desired to form a (hydrocarbylthio)aromatic amine containing fewer hydrocarbylthio groups than a poly(-hydrocarbylthio)aromatic amine in the original reaction mixture.

The process results in the redistribution of hydrocarbylthio substituents on the rings of the aromatic amines with little or no co-formation of secondary or tertiary amines (e.g., amines analogous to the diphenylamine of Thomas, N-alkylanilines, etc.), which, when formed, constitute less than 5 mol %, generally less than 2 mol %, of the reaction products. This is particularly surprising in view of the known preference for Lewis acids to react with amino groups instead of less basic groups such as thioethers.

After completion of the redistribution reaction, the desired (hydrocarbylthio)aromatic amine can be isolated by fractionation. Alternatively, the reaction mixture can be reacted with a suitable hydrocarbyl disulfide to provide additional quantities of the desired (hydrocarbylthio)aromatic amine.

The following examples are given to illustrate the invention and are not intended as a limitation thereof.

EXAMPLE I

A mixture of 13.92 g (0.1 mol) of 2-(methylthio)aniline and 0.893 g (0.0067 mol) of aluminum chloride was stirred at 165°–170° C. in a nitrogen atmosphere for 18 hours. The reaction mixture was cooled, diluted with 50 ml of ether, hydrolyzed with 10 ml of 1N sodium hydroxide, and then extracted with 10 ml of saturated aqueous sodium chloride. The solvent was removed under reduced pressure (40 mm) and the residue distilled (0.35 mm) to give 9.4 g of distillate having a boiling point of 30°–115° C. Analysis by gas chromatography (GC) and mass spectroscopy (MS) showed:

| Compound | Area % |
|---|---|
| aniline | 21 |
| 2-(methylthio)aniline | 58 |
| 4-(methylthio)aniline | 7 |
| 2,4-di(methylthio)aniline | 7 |
| 2,6-di(methylthio)aniline | 6 |

EXAMPLE II

A stirred solution of 13.1 g (0.09 mol) of distilled 2-(methylthio)aniline and 0.84 g (0.006 mol) of aluminum chloride was heated at 175° C. under nitrogen for four hours. An aliquot was taken, cooled, diluted with ether, dried over sodium sulfate, filtered, and concentrated to give 0.9 g of a greenish black liquid. GC analysis using $C_{11}$ and $C_{16}$ hydrocarbons as internal standards gave the following:

| Compound | Wt. % |
|---|---|
| methyl disulfide | 0.4 |
| aniline | 4.9 |
| 2-(methylthio)aniline | 76.6 |
| 3-(methylthio)aniline | none |
| 4-(methylthio)aniline | 0.9 |
| 2,4-di(methylthio)aniline | 7.0 |
| 2,6-di(methylthio)aniline | 3.5* |

*Estimated from area % using the same response factor as 2,4-di(methylthio)aniline

EXAMPLE III

Example II was essentially repeated except that the reaction mixture was heated for 20 hours. The GC analysis showed:

| Compound | Area % | Wt. % |
|---|---|---|
| methyl disulfide | 2 | 1.5 |
| aniline | 22 | 14.9 |
| N—methyl aniline | 1 | |
| 2-(methylthio)aniline | 43 | 38.5 |
| N—methyl-2-(methylthio)aniline | 1 | |
| 3-(methylthio)aniline | 0 | 0.1 |
| 4-(methylthio)aniline | 7 | 6.3 |
| 2,4-di(methylthio)aniline | 8 | 12.1 |
| 2,6-di(methylthio)aniline | 15 | 6.4* |

*Estimated from area % using the same response factor as 2,4-di(methylthio)aniline

EXAMPLE IV

Example III was essentially repeated except that 14.4 g (0.1 mol) of 4-(methylthio)aniline and 0.9 g (0.007 mol) of aluminum chloride were used to produce 14.8 g of product mixture. GC and GC/MS analyses showed:

| Compound | Area % | Wt. % |
|---|---|---|
| methyl disulfide | 2.0 | 1.5 |
| aniline | 20.0 | 16.7 |
| N—methylaniline | 0.4 | |
| 2-(methylthio)aniline | 28.5 | 26.3 |
| N—methyl-2-(methylthio)aniline | 0.4 | |
| 4-(methylthio)aniline | 16.0 | 13.1 |
| N—methyl-4-(methylthio)aniline | 0.3 | |
| 2,6-di(methylthio)aniline | 5.7 | 6.5 (est.) |
| 2,4-di(methylthio)aniline | 22.9 | 18.2 |
| tri(methylthio)aniline | 3.2 | |
| 3-(methylthio)aniline | 0.3 | 0.2 |

COMPARATIVE EXAMPLE

A solution of 14.2 g (0.1 mol) of distilled 3-(methylthio)aniline and 0.9 g (0.007 mol) of aluminum chloride was used to prepare 14.5 g of product mixture by the same general procedure as in Example IV. Analyses of the product mixture showed 96 area % and 89 wt. % of the starting 3-(methylthio)aniline, and distillation provided 12.2 g of the 3-(methylthio)aniline. GC/MS of the pot residue showed 67 area % bis[3-(methylthio)-phenyl]-amine.

It is obvious that many variations can be made in the products and processes set forth above without departing from the spirit and scope of this invention.

What is claimed is:

1. A process which comprises heating a primary carbocyclic aromatic amine having at least one free ring position and at least one hydrocarbylthio substituent in a ring position other than a position meta to the amino group in the presence of a catalyst to redistribute the hydrocarbylthio groups with little or no co-formation of secondary or tertiary amines.

2. The process of claim 1 wherein the aromatic amine is an aminobenzene.

3. The process of claim 2 wherein the aminobenzene is an aniline.

4. The process of claim 1 wherein the aromatic amine is a mixture of anilines.

5. The process of claim 1 wherein the hydrocarbylthio substituents are alkylthio groups.

6. The process of claim 1 wherein the aromatic amine is an (alkylthio)aniline having 1-6 carbons in the alkyl group.

7. The process of claim 1 wherein the catalyst is a metal halide, metal alkyl, or organometallic compound derived by reacting an aromatic amine with a metal halide, metal alkyl, or reactive metal.

8. The process of claim 7 wherein the catalyst is aluminum chloride.

9. The process of claim 1 wherein the reaction is conducted at a temperature of about 100°–300° C.

10. The process of claim 1 wherein an (alkylthio)aniline is heated at 100°–300° C. in the presence of a catalytic amount of aluminum chloride.

11. The process of claim 10 wherein the (alkylthio)aniline has at least one alkylthio group in an ortho-position.

12. The process of claim 10 wherein the (alkylthio)aniline has at least one alkylthio group in a para-position.

* * * * *